United States Patent
Sperling et al.

(10) Patent No.: US 7,567,348 B2
(45) Date of Patent: Jul. 28, 2009

(54) METHOD AND APPARATUS FOR THE EVALUATION OF THE LOCAL SERVERS PROPERTIES OF SURFACES

(75) Inventors: Uwe Sperling, Geretsried (DE); Konrad Lex, Königsdorf (DE)

(73) Assignee: BYK Gardner GmbH, Geretsried (DE)

( * ) Notice: Subject to any disclaimer, the term of this patent is extended or adjusted under 35 U.S.C. 154(b) by 464 days.

(21) Appl. No.: 11/230,316

(22) Filed: Sep. 19, 2005

(65) Prior Publication Data

US 2006/0119854 A1     Jun. 8, 2006

(30) Foreign Application Priority Data

Dec. 8, 2004    (DE)  ............... 10 2004 059 186

(51) Int. Cl.
     *G01N 21/55*      (2006.01)
(52) U.S. Cl. ..................... 356/445; 356/448
(58) Field of Classification Search .......... 356/445–448
See application file for complete search history.

(56) References Cited

U.S. PATENT DOCUMENTS

| | | | | |
|---|---|---|---|---|
| 4,863,268 A | * | 9/1989 | Clarke et al. ............. 356/237.2 |
| 5,583,642 A | * | 12/1996 | Nakazono ................. 356/405 |
| 5,991,037 A | * | 11/1999 | Piel et al. ................. 356/369 |
| 6,166,814 A | * | 12/2000 | Pringle ..................... 356/445 |
| 6,888,632 B2 | * | 5/2005 | Smith ....................... 356/369 |
| 2004/0169859 A1 | * | 9/2004 | Smith ....................... 356/369 |

* cited by examiner

*Primary Examiner*—Michael P Stafira
(74) *Attorney, Agent, or Firm*—Greer, Burns & Crain, Ltd.

(57) ABSTRACT

A method and a device for a spatially resolved examination and evaluation of the properties of surfaces, in particular such properties of surfaces which affect the optical impression which the surface makes. A defined radiation is directed at a first predetermined solid angle to an examined surface. Furthermore, at least a portion of the radiation affected by the examined surface in particular by diffusion and reflection, is detected at a second predefined solid angle. At least one measured variable is spatially resolved captured which characterizes at least one predetermined property of the radiation affected by the examined surface. At least over a portion of the spatially resolved measured values at least one statistical parameter for characterizing the surface is determined.

12 Claims, 3 Drawing Sheets

METHOD AND APPARATUS FOR THE EVALUATION OF THE LOCAL SERVERS PROPERTIES OF SURFACES

BACKGROUND

The present invention relates to a method for the spatially resolved examination and evaluation of surface properties, and in particular, surface properties which affect the optical impression conveyed by a surface. The method will be described below with reference to examining motor vehicle bodies. However, reference is made to the fact that other kinds of surfaces may also be examined with the method of this invention.

Methods for examining surface properties are known from the prior art. Herein light is directed at the examined surface and the light reflected or diffused off the surface is detected and evaluated. This evaluation allows in particular a determination of the optical surface properties such as color or gloss. Such determination or characterization is required since motor-vehicle bodies or their paint coatings convey different impressions to the human eye depending on the surface properties or the incident light and the angle of observation, thus requiring an objective characterization.

Lately, paint coatings have been gaining popularity which comprise pigments or so-called flakes. These pigments or flakes include metal particles statistically distributed in the layer of finish or on its surface. More precisely, metal pigments may consist of very thin metal flakes acting as miniature reflectors.

Characterizing and standardizing these types of finishes or measuring the surface properties of these finishes creates problems since, due to distribution, placement, orientation and sizes or proportions of the pigments or flakes, and depending on the incidence angle of the light, minor variations of the viewing angle may already result in an observer getting different impressions of colors and lightness.

Manufacturers use, among other things, finishes containing interference pigments which, when viewed on large surface areas, result in color gradients at more or less precisely specified color change angles (flop). This may lead to largely different color impressions which in turn leads to varying overall impressions of the lightness or color of the finished surfaces.

These effects and different perceptions of surfaces caused for example by different densities, distribution, compositions and structures of finish additives such as flakes or effect pigments cannot be detected with prior art methods since the respective detection means only supply information on the composite intensity of the light incident from various locations on the measuring surface i.e. they integrate intensity without spatial resolution.

Furthermore, surface properties vary with the location and the observation angle, and prior art methods do not provide feedback to common parameters, in particular not to the parameters of general color theory.

It is therefore the object of the present invention to include in the examination of surface properties, a resolution and evaluation of the different optical impressions caused specifically by location-specific surface properties such as the distribution, placement, and orientation of effect pigments or flakes and observing the surfaces for example, at different solid angles or illumination.

SUMMARY

According to one embodiment, the above object is fulfilled by the method of claim 1 and the device of claim 11. Preferred embodiments and more specific embodiments are the objects of the subclaims.

The method of the invention is useful in that a feedback of surface properties that vary with the location and/or light, to common standardized parameters, established magnitudes of color theory, allows both to more precisely characterize and more easily compare these type of surfaces.

In an embodiment, the method according to the invention provides a predefined radiation directed at an examined surface at a first predefined solid angle.

Furthermore, at least a portion of the radiation affected by the examined surface is detected at a second predefined solid angle wherein at least one measured variable, which characterizes at least one predetermined property of the radiation affected by the examined surface, is captured with spatial resolution.

According to the invention at least a portion of the spatially resolved measured values serves to determine at least one statistical parameter for characterizing the surface.

Radiation affected by the examined surface is understood to mean such radiation which is affected by the examined surface in any one of its properties, in particular by physical effects such as reflection, diffusion, diffraction, absorption and the like and combinations thereof.

A solid angle is understood to be based on the scope of the present invention, as distinguished from the mathematical concept of a solid angle, a tuple of spatial subangles. Herein the first component of the spatial angle, i.e. the first spatial subangle $\alpha$, refers to the projection angle onto the x/z plane relative to the positive z axis of a direction in space defined by a half-line beginning in the origin of a Cartesian coordinate system.

The second component of the solid angle, i.e. the second spatial subangle $\beta$, refers to the projection angle of said half-line to the y/z plane relative to the positive z axis. Herein the coordinate system is oriented such that the measuring surface or at least portions of the measuring surface lie on the x/y plane.

The solid angle is suitable for unambiguously characterizing the orientation of the radiation or detection means relative to the examined surface. A solid angle of (0°, 0°) is understood to mean a solid angle where the radiation or detection means is positioned above the examined surface such that for example the radiation emitting from the radiation means is incident on the examined surface substantially perpendicularly.

A preferred embodiment of the method uses predefined Radiation, which in determining the statistical parameter can be computed back through spectral offset preferably to a standard light type such as in particular A, B, C, D50, D65 D75, F11, TL84 standard light. For determining easily comparable surface parameters it is particularly preferred to use the reference light type D65 which is vital in colorimetry. It is representative of a phase of natural daylight at the color temperature of 6500 Kelvin.

Preferably the property of the radiation affected by the examined surface is selected from a group of properties that includes the spectral radiation intensity, in particular the spectral reflectance $\beta(\lambda)$, the spectral transmission $\tau(\lambda)$, the integral radiation intensity, the wavelength of the radiation intensity maximum and the like.

Within the scope of this invention, spectral reflectance $\beta(\lambda)$ is understood to mean the ratio of the radiation reflected off a portion of the surface compared to the incident radiation, depending on the radiation wavelength $\lambda$ wherein the reflected radiation is measured at a reflection angle opposite that of the incidence angle of the incident radiation.

Within the scope of this invention, spectral transmission $\tau(\lambda)$ is understood to mean the ratio of radiation passing through a portion of the surface compared to the radiation incident on it, depending on the radiation wavelength $\lambda$.

Preferably the at least one captured variable corresponds to at least one of the above-mentioned properties of the radiation affected by the examined surface, and it is particularly preferably proportional. It is also preferred that at least one signal is generated which corresponds to the captured variable, preferably an electric signal which is specifically suitable for the further signal processing of determining the at least one statistical parameter.

In another embodiment of the method, the statistical parameter is determined by using at least one predefined value interval of at least one measured variable. It is preferred that in particular for the optical perception of the surface, substantially irrelevant value intervals may be pre-filtered such as to minimize for example the processing operations for determining the statistical parameter or the surface parameter.

Preferably one determines at least one distribution $F_{m*}$ (m*=m) of the spatially resolved measured values which characterizes the radiation affected. Herein distribution is understood to mean a function where, above predefined measured values in a predetermined value measuring range, the quantity of determined measuring points are plotted which of all spatially resolved measured points contain the respective measured value m.

In another embodiment, at least one parameter characterizing the affected radiation is derived from the spatially resolved—measured values dependent on the at least one statistical parameter, preferably from the at least one distribution $F_{m*}$(m*=m) of the spatially resolved measured values.

In another embodiment the statistical parameter, in particular that of the distribution $F_{m*}$(m*=m) of the spatially resolved measured values, is selected from a group of statistical parameter including the mean value $\mu_{m*}$, the dispersion, the median, the range, the minimum, the maximum, the absolute deviation, the (inter)-quartile range, the standard deviation $\sigma_{m*}$, the variance $\sigma_{m*}^2$ and the like.

In a further embodiment, the mean value $\mu_{m*}$ is selected from a group of mean values including arithmetic, geometric, floating, vectorial, harmonic, weighted, generalized mean values and the like and combinations thereof.

It is preferred to provide in particular for determining the color coordinates of the affected radiation, at least the standard color matching functions $\bar{x}(\lambda)$, $\bar{y}(\lambda)$ and $\bar{z}(\lambda)$, and the emission spectrum $S(\lambda)$ of the incident radiation.

In another embodiment, the spatially resolved spectral reflectance $\beta(x,y,\lambda)$ of the examined surface serves to determine standard spatially resolved tristimulus values $X(x,y) = k\int S(\lambda)\beta(x,y,\lambda)\bar{x}(\lambda)d\lambda$, $Y(x,y) = k\int S(\lambda)\beta(x,y,\lambda)\bar{y}(\lambda)d\lambda$ and $Z(x,y) = k\int S(\lambda)\beta(x,y,\lambda)\bar{z}(\lambda)d\lambda$.

The tristimulus values X, Y and Z unambiguously describe a color as the so-called standard observer will perceive it in defined illumination. However, each of the three tristimulus values only represents the integral of wavelength-dependent individual color stimuli where the composition of the integral value from the values contributed by the individual color stimuli can no longer be established.

The three integrals are decisive for the color perceived wherein the amount of the individual integral contributions is determined by the emission spectrum $S(\lambda)$ of the type of light used and the weighting through the standard color matching distribution functions $\bar{x}(\lambda)$, $\bar{y}(\lambda)$ and $\bar{z}(\lambda)$ of a standard observer, in the observed wavelength interval. Thus in theory an infinite number of different spectral reflectance distributions $\beta(\lambda)$ can produce tristimulus values that are equal though composed of different integral contributions, and thus equal perception—through correspondingly selected emission spectra $S(\lambda)$ of the illumination or other color matching functions $x(\lambda)$, $y(\lambda)$ and $z(\lambda)$ of the observer.

These colors are referred to as "conditionally equal" or "metameric". Metameric colors are perceived as more or less greatly different colors even with equal emission spectra $S(\lambda)$ of the illumination due to the different color matching functions $x(\lambda)$, $y(\lambda)$ and $z(\lambda)$ by different observers. It was among other things this observer-dependent metamerism which has led to establishing the standard observer having standardized color matching functions $\bar{x}(\lambda)$, $\bar{y}(\lambda)$ and $\bar{z}(\lambda)$, such as the 10° standard observer.

Only color pairs having equal spectral reflectance $\beta(\lambda)$ are unconditionally equal or non-metameric—for all observers and all illumination types. Industrial colorimetry and color recipe formulation calculation therefore aim as far as possible at equal reflectance spectra of color reproductions relative to given models. A common parameter is the metamerism index which indicates the color difference between color sample and reproduction when the illumination changes—usually in changing from standard light D65 to standard light A. The metamerism index of the reproduction is usually intended to be low.

Preferably the spatially resolved spectral transmissions $\tau(x,y,\lambda)$ of the examined surface serve to determine standard spatially resolved tristimulus values $X(x,y)=k\int S(\lambda)\tau(x,y,\lambda)\bar{x}(\lambda)d\lambda$, $Y(x,y)=k\int S(\lambda)\tau(x,y,\lambda)\bar{y}(\lambda)d\lambda$ and $Z(x,y)=k\int S(\lambda)\tau(x,y,\lambda)\bar{z}(\lambda)d\lambda$. This serves to determine the standard tristimulus values of at least partially transparent surfaces by transmitted light method.

In an advantageous specific embodiment of the method according to the invention, in particular the standard spatially resolved tristimulus values $X(x,y)$, $Y(x,y)$ and $Z(x,y)$ of the radiation affected by the surface are used to determine spatially resolved CIEL*a*b*-color coordinate values $L^*(x,y)$ $a^*(x,y)$ and $b^*(x,y)$.

A reference of the measured values back to the CIEL*a*b*-color system is advantageous in that it counts among the best known and most widespread, approximately visually equidistant, color systems. The appearance is characterized by the three values L*, a* and b* plotted in a Cartesian coordinate system (see FIG. 3). Neutral "colors" lie on the vertical lightness axis L*. It extends from 0 (black, bottom) to 100 (white, top). With increasing distance from the neutral axis, the color chroma increases. On the a* axis the chromatic color will change from greenish in the negative range to reddish in the positive range, and on the b* axis, the chromatic color will change from bluish in the negative range to yellowish in the positive range. The optimal colors are found at the perimeter of the range. All of the theoretically possible colors are found within the body.

The colors which occur in nature and which can technically be manufactured are clearly within these boundaries. The CIEL*a*b* color space represents a color space where numerically equal differences of the color distances $\Delta E_{AB}=$ $\sqrt{(\Delta L^*)^2+(\Delta a^*)^2+(\Delta b^*)^2}$ with regard to different hues are perceived and evaluated as being virtually equal. The CIEL*a*b* formula (1976) proposed by the CIE represents a compromise over previous formulae between equidistance and tolerable amount of computing operations.

The method of this invention is thus in particular advantageous in the widely used parameters such as metamerism indices or L*a*b color coordinates can be determined also for surfaces whose color effects vary with shifting locations or angles.

In another embodiment, the standard spatially resolved tristimulus values X(x,y), Y(x,y) and Z(x,y) of the radiation affected by the surface are used to determine spatially resolved CIEL*C*H* color coordinate values L*(x,y), C*(x,y) and h*(x,y).

The CIEL*C*H* color space is not an additional color space. Instead of the Cartesian coordinates a*, b* the polar coordinates C* and h* are used wherein the lightness value L* is likewise used. Color type and color saturation are defined in said color space through the chromatic color angle h* and the distance C* from the neutral axis which is referred to as chroma or saturation.

Alternatively, another embodiment provides that the spatially resolved standard tristimulus values X(x,y), Y(x,y) and Z(x,y) of the radiation affected by the surface serve in particular to determine spatially resolved CIEL*u*v* color coordinate values L*(x,y), u*(x,y) and v*(x,y).

Preferably the spatially resolved CIE color coordinate values are used to determine CIE color coordinate value distributions, preferably CIEL*a*b* color coordinate value distributions $F_{L^*}(L^*=L)$ $F_{a^*}(a^*=a)$ and $F_{b^*}(b^*=b)$.

In another embodiment, at least one statistical parameter of the CIE color coordinate value distributions, preferably of the CIEL*a*b* color coordinate value distributions $F_{L^*}(L^*=L)$ $F_{a^*}(a^*=a)$, and $F_{b^*}(b^*=b)$ is determined which is selected from a group of statistical parameters including the mean value, the dispersion, the median, the range, the minimum, the maximum, the absolute deviation, the (inter)-quartile range, the standard deviation, the variance, and the like.

In a further embodiment, the first and/or the second predefined solid angle is changed at least once, the radiation affected by the examined surface is re-detected and the at least one statistical parameter is re-determined. This allows easy determination of the distribution of color and lightness of the examined surface which varies with the location—such as due to flakes or effect pigments—even at different observing angles, and sensing the surface at different angles.

The invention further relates to a device for employing the method of the invention for determining the properties of surfaces.

The device according to the invention provides at least one first radiation device which directs a predefined radiation at an examined surface at a first predefined solid angle.

Furthermore, the device according to the invention comprises at least one first detection means which detects at a second predefined solid angle at least a portion of the radiation affected by the examined surface wherein at least one measured variable, which characterizes at least one defined property of the radiation affected by the examined surface, is captured with spatial resolution.

According to the invention at least one processor device is further provided to determine at least one statistical parameter over at least a portion of the spatially resolved measured values for characterizing the surface.

Furthermore, the device according to the invention comprises at least one output device which outputs at least the statistical parameter or a parameter derived therefrom or at least from the spatially resolved measured values.

In an embodiment, the first detection means comprises at least one preferably plane image-capturing component which allows the spatially resolved detection of radiation.

In another embodiment, the first detection means is selected from a group of detection means comprising cameras, CCD chips and the like.

In an embodiment, at least one second radiation means is provided.

In another embodiment, at least two radiation means emit radiation to the examined surface concurrently, at least intermittently.

In further embodiment, at least one of the radiation means comprises at least one radiation source from a group of radiation sources including light bulbs, gas discharge lamps, halogen lamps, light-emitting diodes, lasers and laser diodes, thermal radiation sources and the like.

In another embodiment, at least one radiation source is variable in at least one radiative characteristic such as in particular but not exclusively the emission spectrum $S(\lambda)$, the wavelength of the intensity maximum, polarization, intensity, modulation, coherence, or the like.

In an embodiment, at least one radiation source emits radiation which in determining the statistical parameter can be computed back preferably to a standard light type such as in particular A, B, C, D50, D65 D75, F11, TL84 standard light, and particularly preferably to D65 standard light.

In a further embodiment, at least one second detection means is provided which is selected from a group of detection means including photo cells, photo elements, photo diodes, and the like. This allows in addition to spatially resolved, also spacially integrated measuring.

In another embodiment, the radiation means and the detection means are positioned in one common housing that is substantially opaque to radiation and comprises at least one aperture through which radiation is channeled onto the examined surface.

In a further embodiment, at least one memory means is provided to store, in particular for determining color coordinates of the affected radiation, at least the standard color matching functions $\bar{x}(\lambda)$, $\bar{y}(\lambda)$ and $\bar{z}(\lambda)$, and the emission spectrum $S(\lambda)$ of the incident radiation.

The method of the invention and the device of the invention are used to determine in particular spatially resolved surface properties, preferably the surface properties of paint coatings of motor vehicles.

Other advantages and embodiments of the present invention can be taken from the following description of preferred embodiments and the accompanying drawings.

DETAILED DESCRIPTION

Figure 1:
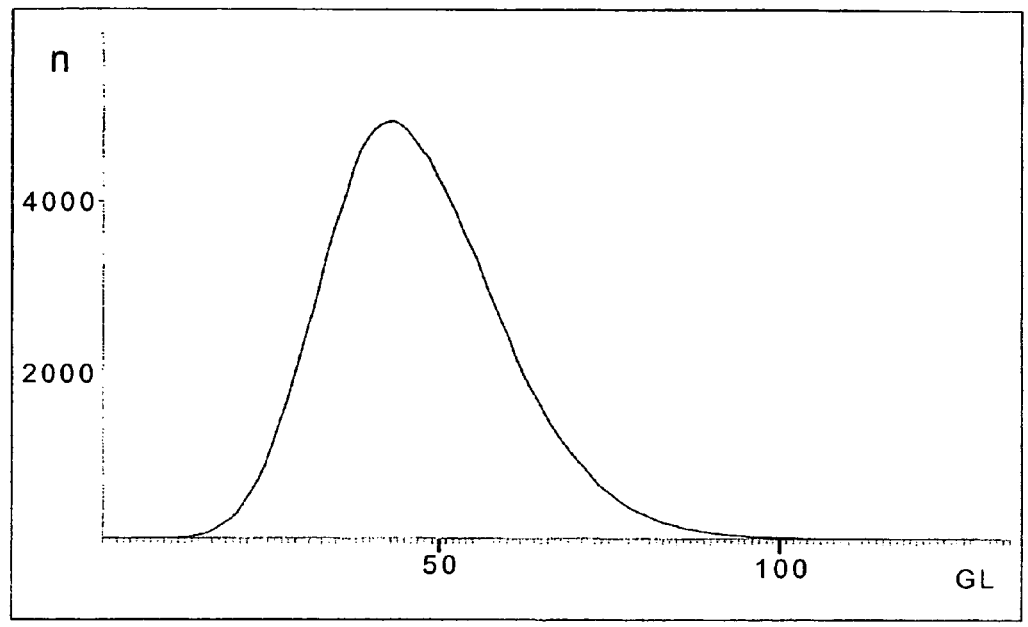
FIG. 1 a diagram of the distribution of the quantity of flakes in an effect paint coating at a specific lightness determined by means of the spatially resolved method of the invention.

The diagram illustrated in FIG. 1 shows the result of the method of the invention for spatially resolved examination of surface properties of a surface provided with an effect paint coating.

For this purpose a predefined radiation is directed at the examined surface at a first solid angle ($\alpha_1$; $\beta_1$).

A portion of the radiation reflected and/or diffused off the examined surface is detected at a second predefined solid angle. In the present case, the spatially resolved lightness that results in particular from the different orientations of the flakes is captured in integer grey level values (Grey Level, GL) as a spatially resolved measured variable. The lightness of the reflected radiation thus forms the predetermined property of the radiation affected by the examined surface.

According to an embodiment, the spatially resolved grey level measured values are used to determine the distribution illustrated in the diagram of the number n of flakes at a specific grey level GL as a statistical parameter for characterizing the surface.

Figure 2:
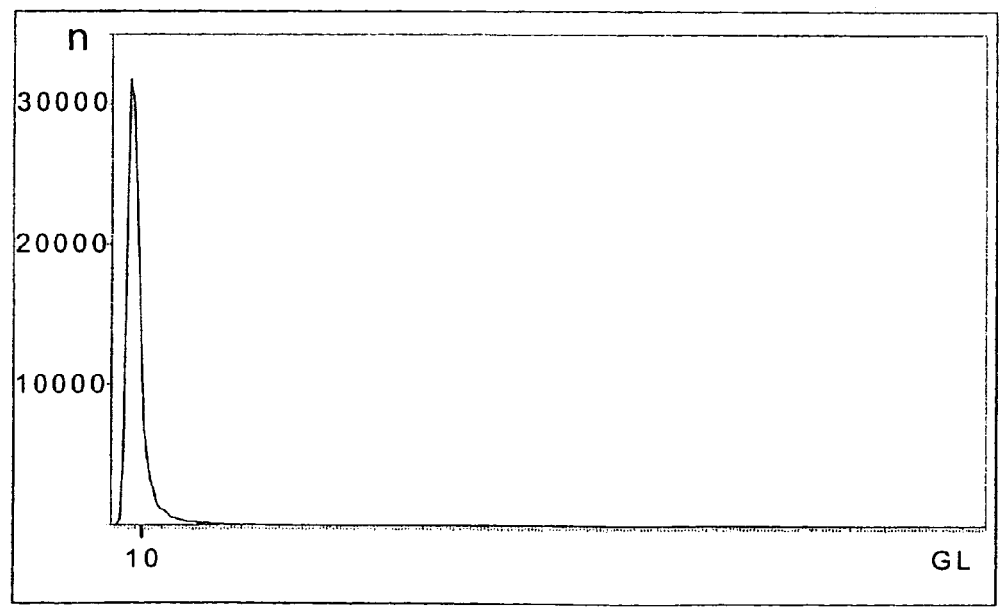
FIG. 2 a diagram of another distribution of the quantity of flakes at a specific lightness determined by means of the spatially resolved method of the invention.

FIG. 2 shows the distribution of the number n of flakes at a specific grey level GL for illumination at a different solid angle ($\alpha_2$; $\beta_2$). The lightness or grey level in FIG. 2 is clearly better defined i.e. the majority of the number of flakes reflects radiation of substantially the same lightness.

Figure 3:
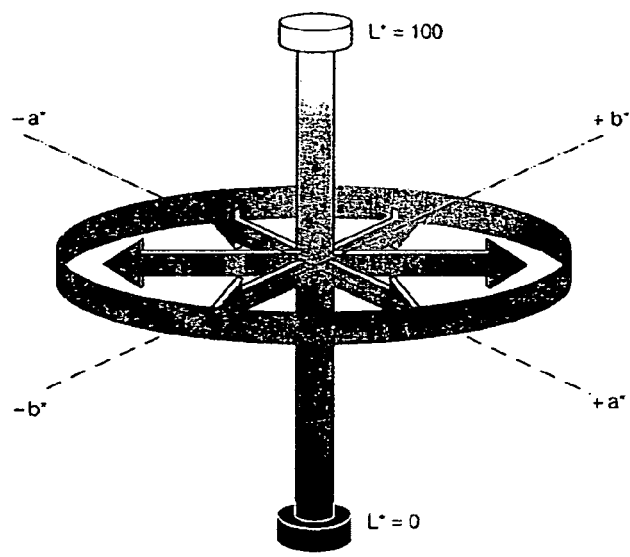
FIG. 3 an illustration of the CIEL*a*b color coordinate system.

FIG. 3 is an illustration of the CIEL*a*b color coordinate system explained above. The hue is described therein by the three coordinates L*, a*, and b* plotted in the Cartesian coordinate system illustrated. The vertical axis of lightness L* comprises neutral "colors" or grey levels which extend from black below, labeled 0, to white above, labeled 100. An increasing distance from the neutral axis corresponds to increasing color chroma. On the a* axis the chromatic color will change from greenish in the negative range to reddish in the positive range, and on the b* axis, the chromatic color will change from bluish in the negative range to yellowish in the positive range.

Figure 4:
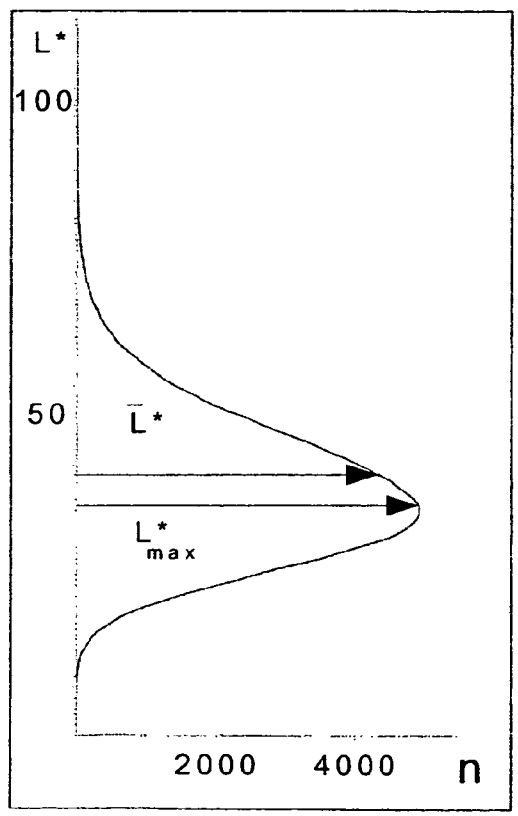
FIG. 4 a diagram of the distribution of the quantity of flakes at a specific L* lightness coordinate value determined by means of the locus-spatially resolved of the invention.

FIG. 4 finally shows another diagram as a product of the method of the invention. Therein detection has spatially resolved captured the spectral reflectance $\beta(x,y,\lambda)$ for example in the wavelength range between 380 and 720 nm. These in turn serve as the basis for a spatially resolved determination of the standard tristimulus values X(x,y), Y(x,y) and Z(x,y), which finally allow determination of spatially resolved CIEL*a*b* color coordinate values L*(x,y), a*(x,y) and b*(x,y).

According to a preferred specific embodiment of the method of the invention the illustrated CIEL*a*b* color coordinate value distribution $F_{L*}(L*=L)$ has been determined for all of the L*(x,y). In the example the number n of flakes at a specific L* value is illustrated as a statistical parameter for characterizing the surface. One can determine from the distribution $F_{L*}(L*=L)$ for example the mean L* value $\overline{L}*$ or the maximum L* value $L*_{max}$ of all spatially resolved L* values.

These for example, in combination with the respective sensed mean $\overline{a}*$ and $\overline{b}*$ values are suitable for a preferred characterization of the effect paint coating. More specific surface parameters are likewise conceivable for assessing color blending dependent on the observation angle, for example by means of weighted averaging of the mean $\overline{L}*$, $\overline{a}*$ and $\overline{b}*$ values captured across an angle range.

Figure 5:
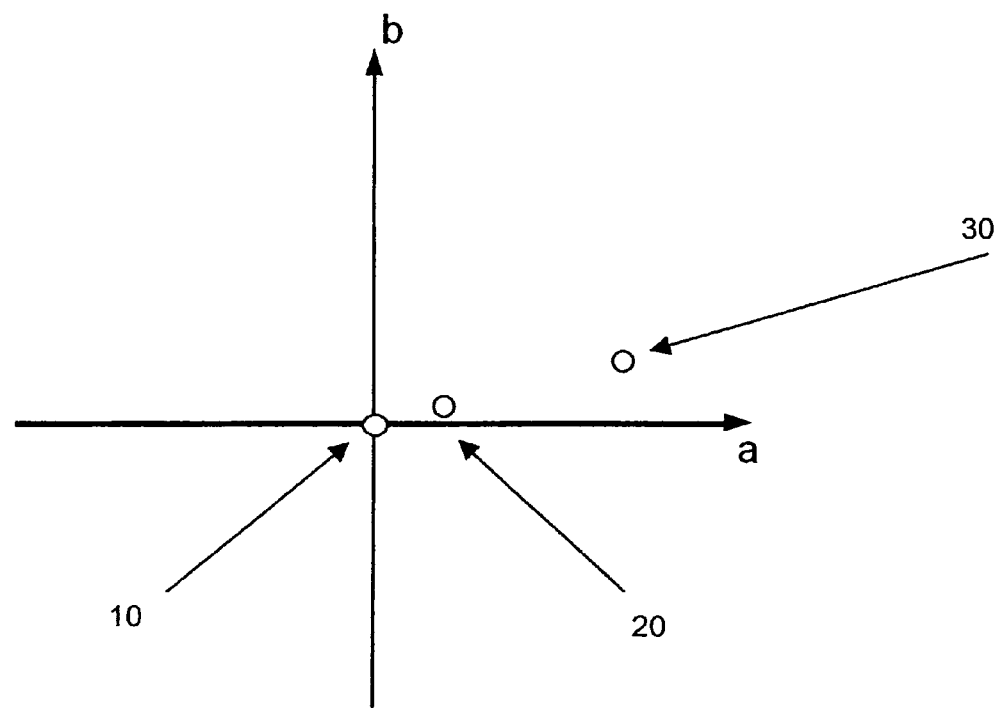
FIG. 5 a diagram showing the relevance of spatial resolution for color measuring for a black topcoat including red effect pigments.

To illustrate the relevance of spatial resolution for color measuring, FIG. 5 shows an a* b* diagram for a black topcoat including red effect pigments. The lightness value L* plays a secondary role in this example. In FIG. 5 the reference numeral 10 indicates the color locus of the black topcoat and the reference numeral 30, the color locus of the red effect pigments.

The reference numeral 20 indicates the color locus determined on the basis of spatially integrated color measuring, of the black topcoat with the red effect pigments. In respect of the visual perception of this paint coating the integral measuring method will, due to the inherent averaging of the color locus for the topcoat and for the effect pigments, indicate the "wrong" color locus of a color which the eye would perceive as black with a slightly reddish tint. Actually, however, the eye will perceive the finish as black with red "sparkles".

If this visual impression is to be captured by measuring, the color locus of topcoat and effect pigments must be captured separately, i.e. separated as to their physical location. The color values or chrominance thus separately determined for topcoat and effect pigments are preferably evaluated in the CIEL*a*b color coordinate system or in another of the color coordinate systems indicated above since the contrast values so determined largely correlate with visual color perception. It is thus possible to numerically specify the visual contrast of the red effect pigments relative to the black topcoat in the corresponding color coordinate system.

The color value of a topcoat is also referred to as base code. Thus only the spatially resolved determination of CIEL*a*b* color coordinate values L*(x,y), a*(x,y) and b*(x,y) allows a correct determination of the base code of topcoats containing effect color pigments which displace and thus adulterate the actual visual impression of a color value determined by integral measurement.

Furthermore, the visually perceived contrast values depend on the illumination. Color contrast may be evaluated differently in natural light and in artificial light. The difference of contrast values can be computed employing standard light types.

On the whole the effect paint example in FIG. 5 makes it evident that a spatially resolved evaluation is required of the color impression of surfaces under illumination by a predetermined standard light type according to standard distribution functions so as to obtain a dimension of how the individual components of the surface color harmonize or what color contrast is perceived. The spatially resolved color measurement of the invention allows the desired precision in measured capturing the visual impression that a human receives from a surface.

Figure 6:
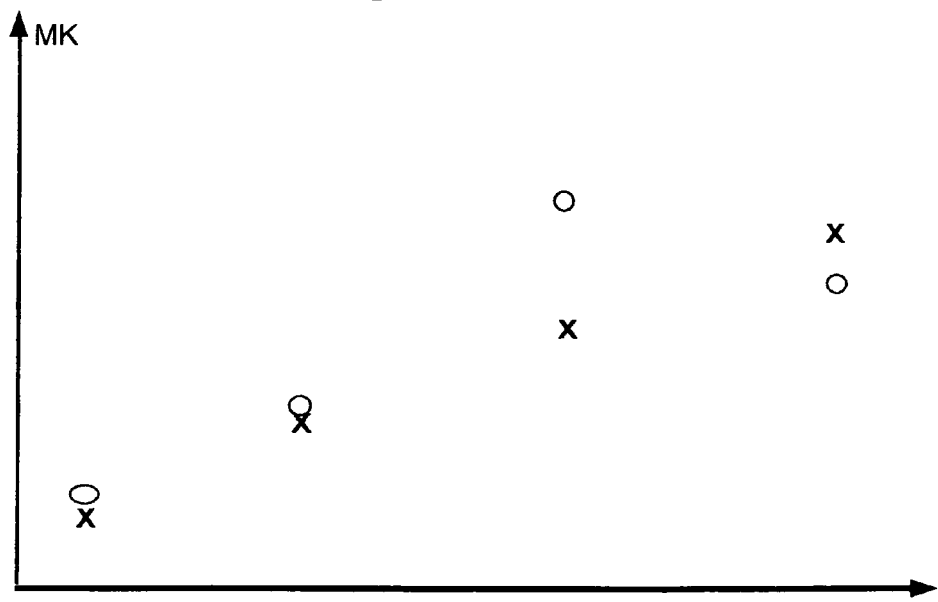
FIG. 6 a diagram showing an example of the effect of non-standard light on the relationship between visually perceived contrast (VK) and measured contrast (MK).

In this conjunction, FIG. 6 shows an example of the effect which use of non-standard light can have on the relation of measured to visual impression of a contrast. Therein four color panels having base paint coatings in different colors and containing additional effect pigments are assessed as to inhomogeneity or roughness of the finish (also called texture). This can originate among other things from a preferred orientation or an inhomogeneous distribution of the effect pigments in the paint coat.

The measuring points designated "x" refer to four test panels measured under standard light type D65 and evaluated visually. The measured values substantially lie on a straight line. This means that a change in the visually perceived contrast "VK" plotted toward the right, results in a change in the measured contrast "MK" plotted upwardly, i.e. visual impression and measurement correlate well with one another.

The measuring points designated "o" refer to four test panels measured not under standard light but under unfiltered light from an LED and evaluated visually. The third measured value from the left in particular shows that a correlation between the measured contrast "MK" and the visually perceived contrast "VK" is no longer present under the unfiltered LED illumination.

The invention claimed is:

1. A method for examining optical surface properties, in particular for spatially resolved determination of surface properties including the steps:
   directing a predetermined radiation at a first predetermined solid angle at an examined surface; and
   detecting at least a portion of the radiation affected by the examined surface a second predetermined solid angle wherein at least one measured variable, which characterizes at least one predefined property of the radiation affected by the examined surface is captured with spatial resolution;
   determining at least one statistical parameter over at least a portion of the spatially resolution measured values for characterizing the surface,
   wherein in determining the at least one statistical parameter, the predetermined radiation can be computed back preferably to a standard light type such as in particular A, B, C, D50, D65, D75, F11, TL84 standard light, and particularly preferably to D65 standard light.

2. The method of claim 1, wherein the property of the radiation affected by the examined surface is selected from a group of properties that includes the spectral radiation intensity, in particular the spectral reflectance $\beta(\lambda)$, the spectral transmission $\tau(\lambda)$, the integral radiation intensity, the wavelength of the radiation intensity maximum and the like.

3. The method of claim 1, wherein the statistical parameter is determined using at least one predetermined value interval of at least one measured variable.

4. The method of claim 1, wherein at least one distribution $F_{m*}(m^*=m)$ of the spatially resolved measured values which characterizes the radiation affected, is determined.

5. The method of claim 1 wherein at least one parameter characterizing the affected radiation is derived from the spatially resolved measured values dependent on the at least one statistical parameter, preferably from the at least one distribution $F_{m*}(m^*=m)$ of the spatially resolved measured values.

6. The method of claim 5, wherein the statistical parameter, in particular that of the distribution $F_{m*}(m^*=m)$ of the spatially resolved-measured values, is selected from a group of statistical parameters including the mean value $\mu_{m*}$, the dispersion, the median, the range, the minimum, the maximum, the absolute deviation, the (inter)-quartile range, the standard deviation $\sigma_{m*}$, the variance $\sigma2_{m*}$ and the like.

7. The method of claim 6, wherein the mean value $\mu_{m*}$ is selected from a group of mean values including arithmetic, geometric, floating, vectorial, harmonic, weighted, generalized mean values and the like and combinations thereof.

8. The method of claim 1, particular for determining the color coordinates of the affected radiation, at least the standard color matching functions $\bar{x}(\lambda)$, $\bar{y}(\lambda)$ and $\bar{z}(\lambda)$, and the emission spectrum $S(\lambda)$ of the incident radiation, are provided.

9. The method of claim 1, wherein the first and/or the second defined solid angle are changed at least once, the radiation affected by the examined surface is re-detected by the detection means and at least one statistical parameter is re-determined.

10. Application of the method of claim 1 for determining the properties, in particular spatially resolved properties, of surfaces, preferably the properties of surfaces of motor vehicle paintings.

11. A device for performing the method of claim 1 including the steps of:
   directing a predetermined radiation at a first predetermined solid angle at an examined surface; and
   detecting at least a portion of the radiation affected by the examined surface at a second predetermined solid angle wherein at least one measured variable, which characterizes at least one predefined property of the radiation affected by the examined surface is captured with spatial resolution;
   determining at least one statistical parameter over at least a portion of the spatially resolution measured values for characterizing the surface.

12. A method for examining optical surface properties, in particular for spatially resolved determination of surface properties including the steps:
   directing a predetermined radiation at a first predetermined solid angle at an examined surface;
   detecting at least a portion of the radiation affected by the examined surface at a second predetermined solid angle wherein at least one measured variable, which characterizes at least one predefined property of the radiation affected by the examined surface is captured with spatial resolution;
   determining at least one statistical parameter over at least a portion of the spatially resolution measured values for characterizing the surface; and
   deriving at least one parameter characterizing the affected radiation from the spatially resolved measured values dependent on said at least one statistical parameter,
   wherein in determining the at least one statistical parameter, the predetermined radiation can be computed back preferably to a standard light type such as in particular A, B, C, D50, D65, D75, F11, TL84 standard light, and particularly preferably to D65 standard light.

* * * * *